United States Patent [19]
Olson

[11] Patent Number: 5,205,283
[45] Date of Patent: Apr. 27, 1993

[54] METHOD AND APPARATUS FOR TACHYARRHYTHMIA DETECTION AND TREATMENT

[75] Inventor: Walter H. Olson, North Oaks, Minn.

[73] Assignee: Medtronic, Inc., Minneapolis, Minn.

[21] Appl. No.: 737,947

[22] Filed: Jul. 30, 1991

[51] Int. Cl.$^5$ .......................... A61N 1/368; A61B 5/04
[52] U.S. Cl. .............................. 128/419 PG; 128/705; 128/419 D
[58] Field of Search ............. 128/419 PG, 419 D, 705

[56] References Cited

U.S. PATENT DOCUMENTS

| | | |
|---|---|---|
| Re. 27,757 | 3/1987 | Mirowski . |
| 3,832,994 | 9/1974 | Bicher et al. ....................... 128/705 |
| 3,857,399 | 12/1974 | Zacouto . |
| 4,384,585 | 5/1983 | Zipes . |
| 4,523,595 | 6/1985 | Zibell . |
| 4,577,634 | 3/1986 | Gessman . |
| 4,712,554 | 12/1987 | Garson, Jr. . |
| 4,754,753 | 7/1988 | King . |
| 4,790,317 | 12/1988 | Davies . |
| 4,860,749 | 8/1989 | Lehmann ...................... 128/419 PG |
| 5,107,850 | 4/1992 | Olive ................................. 128/705 |

OTHER PUBLICATIONS

Automatic Tachycardia Recognition by R. Arzbaecher et al. PACE, May-Jun. 1984, pp. 541-547.
Necessity of Signal Processing in Tachycardia Detection by Furman et al., in: The Third Decade of Cardiac Pacing: Advances in Technology in Clinical Application, 1982.
Automatic Implantable Cardioverter-Defibrillator Structural Characteristics, PACE, vol. 7, Nov. Dec., 1984, Part II, pp. 1331-1334 by Mower et al.
Experiment Alventricular Defibrillation With an Automatic and Completely Implanted System, by Schuder et al. in American Society of Artificial Internal Organs, 1970.
Implantable Pacers for Tachycardia Terminations Stimulation Techniques and Long-Term Efficacy, by Fisher et al., PACE vol. 9, Nov. Dec. 9, 1986 1069-1078.
Changes in Spontaneous Sinus Node Rate as an Estimate of Cardiac Autonomic Tone During Stable and Unstable Ventricular Tachycardia by Huikuri et al., American College of Cardiology, 1989.

Primary Examiner—Kyle L. Howell
Assistant Examiner—Kennedy J. Schaetzle
Attorney, Agent, or Firm—Harold R. Patton; Reed A. Duthler

[57] ABSTRACT

An implantable cardioverter capable of delivering pacing and cardioversion level therapies. The device distinguishes between stable and unstable ventricular tachyarrhythmias by monitoring the progression of atrial cycle lengths during the detected ventricular tachyarrhythmia. A detected increase in atrial cycle lengths during the early stages of the detected ventricular tachycardia is taken as an indication of hemodynamically unstable ventricular tachycardia.

18 Claims, 3 Drawing Sheets

METHOD AND APPARATUS FOR TACHYARRHYTHMIA DETECTION AND TREATMENT

BACKGROUND OF THE INVENTION

This invention relates to automatic implantable devices to detect and differentiate between tachycardias (rapid heart rhythms) in order to therapeutically stimulate the heart in response thereto, and more specifically, to distinguish hemodynamically stable and unstable ventricular tachycardias and provide appropriate treatments for the both.

Early automatic tachycardia detection systems for automatic implantable cardioverter defibrillators relied upon the presence or absence of electrical and mechanical heart activity (such as intramyocardial pressure, blood pressure, impedance, stroke volume or heart movement) and or the rate of the electrocardiogram. For example, the 1961 pamphlet by Dr. Fred Zacouto, Paris, France, entitled, "Traitement D'Urgence des Differents Types de Syncopes Cardiaques du Syndrome de Morgangni-AdamsStokes" (National Library of Medicine) describes an automatic pacemaker and defibrillator responsive to the presence or absence of the patient's blood pressure in conjunction with the rate of the patient's electrocardiogram. Later detection algorithms proposed by Satinsky, "Heart Monitor Automatically Activates Defibrillator", *Medical Tribune*, 9, No. 91:3, Nov. 11, 1968, and Shuder et al "Experimental Ventricular Defibrillation with an Automatic and Completely Implanted System", *Transactions American Society for Artificial Internal Organs*, 16:207, 1970, automatically detected and triggered defibrillation when the amplitude of the R-wave of the electrocardiogram fell below a predetermined threshold over a predetermined period of time. The initial system proposed by Mirowski et al in U.S. Pat. No. 27,757, similarly relied upon the decrease in the amplitude of a pulsatile right ventricular pressure signal below a threshold over a predetermined period of time, was abandoned by Mirowski et al in favor of the rate and/or probability density function morphology discrimination as described in Mower et al, "Automatic Implantable Cardioverter-Defibrillator Structural Characteristics", *PACE*, Vol. 7, November–December 1984, Part II, pp. 1331–1334. Others have suggested the use of high rate plus acceleration of rate "onset" (U.S. Pat. No. 4,384,585) with sustained high rate and rate stability (U.S. Pat. No. 4,523,595).

Very generally, the systems that depend upon the aforementioned criteria are capable of discriminating ventricular tachycardia in greater or lesser degree from normal heart rate but have difficulty discriminating sinus or other supraventricular tachycardias from malignant, pathologic ventricular tachycardias, resulting in inappropriate cardiac electrical stimulation.

As stated in the article "Automatic Tachycardia Recognition" by R. Arzbaecher et al, *PACE*, May–June 1984, pp. 541–547, anti-tachycardia pacemakers that were undergoing clinical studies prior to the publication of that article detected tachycardia by sensing a high rate in the chamber to be paced. The specific criteria to be met before pace termination was to be attempted involved a comparison of the detected rate to a preset threshold, such as 150 beats per minute (400 millisecond cycle length) for a preselected number of beats. As stated above, other researchers had suggested the rate of change of rate or suddenness of onset, rate stability and sustained high rate as additional criteria to distinguish sinus tachycardias from malignant ventricular tachycardias. Arzbaecher et al proposed in their article an algorithm implemented in a microprocessor based implantable device employing both atrial and ventricular rate detection via separate bipolar leads in order to detect the AA and VA, or VV and AV intervals (in "cycle lengths") against threshold intervals in order to distinguish among various types of tachycardias. The Arzbaecher et al article also discloses the concept of employing a single atrial extra stimulus to distinguish sinus tachycardia from 1:1 paroxysmal tachycardia. An atrial extra stimulus was delivered in late diastole (80 milliseconds premature), and if the ventricular response appeared early as well, sinus rhythm would be indicated. However, in tachycardias, such as AV reentrant and ventricular with VA conduction, the ventricular response would not occur early (indicating that the atrial and ventricular rhythms were disassociated) and the ventricular rhythm would be unperturbed.

Other proposals for employing atrial and ventricular detection and interval comparison are set forth in The Third Decade of Cardiac Pacing: Advances in Technology in Clinical Applications, Part III, Chapter 1, "Necessity of Signal Processing in Tachycardia Detection" by Furman et al (edited by S. Barold and J. Mugica, Futura Publications, 1982, pages 265–274) and in the Lehmann U.S. Pat. No. 4,860,749. In both cases, atrial and ventricular rates or intervals are compared to one another in order to distinguish sinus and pathological tachycardias.

The reliable distinction of sinus tachycardia from pathologic tachycardias remains a major limitation of even those systems and algorithms that have been proposed employing both atrial and ventricular detection and interval discrimination as described above. Many paroxysmal tachycardias are initiated by isolated premature beats. The tachycardias may reach a stabilized rate only after a number of beats. By contrast, some sinus tachycardias may mimic paroxysmal tachycardias in their abrupt initiation. Moreover, ventricular tachycardias can be either hemodynamically stable or unstable. Hemodynamically stable ventricular tachycardias exhibit monomorphic constant cycle lengths without loss of consciousness. Hemodynamically unstable ventricular tachycardias may also exhibit constant cycle lengths but result in loss of consciousness and therefore require a more rapid termination, for example by means of a cardioversion pulse. Stable tachycardias do not require termination as quickly, allowing for use of less aggressive treatments such as antitachycardia pacing to attempt termination before employing cardioversion shocks.

Accordingly, it is an objective of the present invention to provide an improved medical device for treating ventricular tachyarrhythmias, including ventricular tachycardia, flutter, and fibrillation with improved techniques for distinguishing hemodynamically stable ventricular tachycardias from hemodynamically unstable ventricular tachycardias and applying appropriate therapies.

SUMMARY OF THE INVENTION

In the context of an automatic implantable device for treating bradyarrhythmias, tachyarrhythmias and fibrillation, the present invention comprises a method and apparatus for distinguishing hemodynamically stable and hemodynamically unstable ventricular tachycardias. The apparatus is provided with means for sensing the atrial electrocardiogram and the ventricular electrocardiograms, for deriving atrial and ventricular cycle lengths (ACL and VCL, respectively) from the respective atrial and ventricular electrocardiograms, determining whether the ventricular cycle lengths reflect a ventricular rate exceeding a preset tachycardia rate threshold.

If the ventricular rate indicates the presence of a tachycardia, the device determines whether the atrial cycle length tends to shorten for an initial number of intervals or period of time following the confirmation that a tachycardia has commenced, and then determines whether the atrial cycle length continues to shorten or lengthens for a second time period following the initial time period. If the atrial cycle length continues to shorten in the second time period, the tachycardia is classified as stable. In the event that the atrial intervals lengthen in the second time period, the tachycardia is classified as unstable.

If the tachycardia is classified as unstable, the apparatus delivers cardioversion or defibrillation therapies. However, if the tachycardia is classified as stable, the apparatus delivers a different therapy, such as one or more of the known pacing stimulation regimens for the treatment of atrial and ventricular tachycardias.

It should be noted that the present invention does not provide a method of distinguishing stable from unstable ventricular tachycardia in those circumstances in which 1:1 V-A conduction persists during the tachyarrhythmia and overdrives the atrium's intrinsic rate. For this reason, the invention is disclosed as activated primarily in those circumstances in which the atrial rate is less than the ventricular rate. The invention is preferably not employed simultaneously with pacing modes which include atrial pacing functions, as such pacing would in some cases interfere with measurement of intrinsic atrial cycle lengths.

It is contemplated that the method of the present invention will be performed when the ventricular rhythm satisfies the rate, onset and other tachycardia detection criteria, but the atrial rate does not exhibit 1:1 tracking. Thus, ventricular tachycardia has been detected and the therapy decision depends upon the behavior of the atrial rate. If the atrial rate steadily increases (the atrial cycle length decreases) over the first twenty seconds of the VT episode, it is concluded that the ventricular tachycardia is stable. However, if the atrial rate increases (atrial cycle length decreases), during about the first ten seconds after onset of the tachycardia and then decreases during the next ten seconds, the ventricular tachycardia is deemed unstable. As stated earlier, different therapies and different therapy regimens of one or more successive therapies would be provided for stable ventricular tachycardia than for unstable ventricular tachycardia.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

Figure 1:
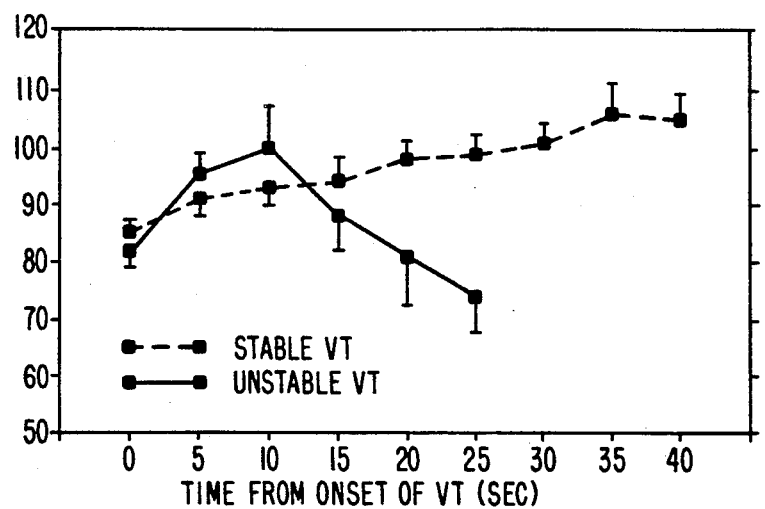
FIG. 1 is a graphic diagram illustrating the changes in sinus rate as a function of time from onset during hemodynamically stable ventricular tachycardia and hemodynamically unstable ventricular tachycardia.

An understanding of the operational mode of the present invention is facilitated by a brief discussion of the physiology of the heart and the theoretical mechanisms of reentrant tachycardias.

The normal pumping action of the heart results from highly organized electrical activity in the cardiac tissue. Each natural spontaneous heart beat begins with an electrical discharge from the sino-atrial node (S-A). located in the right atrium of the heart. This electrical impulse is conducted through tissues which result in the progressive depolarization of the atrial tissue causing it to contract. The contraction forces blood from the atrium through the heart valves into the ventricles. The electrical impulse from the atrium is communicated to the ventricles through the atrio-ventricular node (A-V), which is located on the septal wall dividing the right and left heart. The electrical signal is delayed in this conductive mode for approximately 0.15 seconds and is then transmitted through the His bundle and its branches to the Purkinje fibers which discharge ventricular muscle, causing the ventricles to contract in an organized fashion and pump blood throughout the body. In the healthy heart, this normal sinus rhythm may be repeated between 60 and 120 times per minute. In the diseased heart, however, a number of arrhythmias may occur which disrupt this normal activity. The type of arrhythmias are divided into two groups: tachyarrhythmias, which are generally characterized by heart rates faster than normal, and bradyarrhythmias, which are characterized by heart rates lower than normal.

Tachyarrhythmias may be characterized further by their location of origin. For example, the origin of supraventricular tachyarrhythmias is atrial or nodal; and their maintenance involves the atria and sometimes ventricles. Ventricular tachyarrhythmias originate and are maintained within the ventricles and sometimes conduct to the atria.

A separate group of tachyarrhythmias are called flutter or fibrillation. Flutter is generally characterized by rapid, organized heart activity and, when involving the ventricles, low cardiac output. Fibrillation is characterized by highly disorganized electrical activity that results in virtually no cardiac output when it involves the ventricles. In some patients there may be a progression from an organized tachycardia to fibrillation which will lead to death if the site of the fibrillation is the ventricles. In many patients, ventricular tachycardia precedes the onset of ventricular fibrillation; and if the former can be terminated, generally with small amounts of energies, the latter can be prevented. Some patients exhibit chronic atrial flutter or fibrillation which may be debilitating but does not cause death, and other patients exhibit occasional or paroxysmal attacks of ventricular tachycardias which require cardioversion. See, for example, "Cardiac Arrhythmias," in *Current Diagnosis*, W. B. Saunders Co., 1977, pp. 377-396, by Douglas P. Zipes, M.D.

Ventricular tachycardias can often be converted to sinus rhythm by the application of cardioversion shock or by the application of pacing energy electrical stimulation including rate adaptive or orthorhythmic stimulation as described first in Zacouto U.S. Pat. No. 3,857,399, overdrive stimulation, burst overdrive stimulation rate scanning or any of the other known pacing therapies as described, for example, in Fisher et al, "Implantable Pacers for Tachycardia Termination: Stimulation Techniques and Long-Term Efficacy", *PACE*, Vol. 9, November–December 1986, Part 11, pp. 1325-1333.

As a general proposition, it is preferable to convert ventricular tachycardias, if possible, to sinus rhythm by application of lower energy stimulation in order to conserve energy of the power sources of the implantable device as well as to maintain patient comfort. Man patients cannot tolerate the pain associated with cardioversion or defibrillation shock therapies leading to dread of the implanted cardioverter/defibrillator. Thus, if appropriate, it is desirable to first attempt to restore sinus rhythm through the application of pacing energy therapies of one or more of the types described above.

As noted above, some ventricular tachycardias are hemodynamically stable, producing a cardiac output at least sufficient to maintain consciousness. In these circumstances, one or more attempts to terminate the tachycardia by means of pacing level therapies may be appropriate. Hemodynamically unstable ventricular tachycardias, in contrast, result in a substantial reduction of cardiac output which, if uncorrected, can lead quickly to unconsciousness and subsequent serious injury or death due to lack of blood flow. Immediate delivery of cardioversion shocks may be more appropriate than attempting antitachycardia pacing in these cases, in order to terminate the tachycardia as quickly as possible.

In the article entitled "Changes in Spontaneous Sinus Node Rate as an Estimate of Cardiac Autonomic Tone During Stable and Unstable Ventricular Tachycardia", appearing in *JACC*, Vol. 15, No. 3, Mar. 1, 1989, pp. 646-651, the authors (Heikki V. Huikuri, M.D. et al) describe the characteristics of stable and unstable ventricular tachycardia. Huikuri et al studied sinus rate during induced ventricular tachycardia, not conducted to the atrium, and compared changes of sinus rate during hemodynamically stable and unstable tachycardia. Huikuri et al terminated episodes of stable and unstable ventricular tachycardia exclusively with cardioversion shock therapies.

Figure 3:
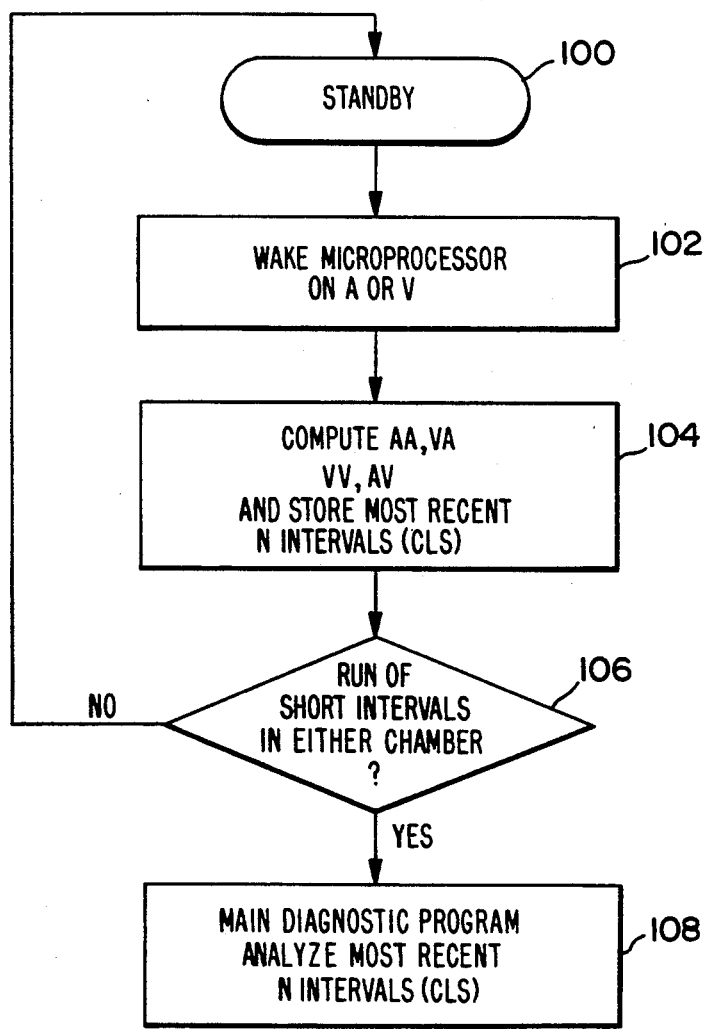
FIG. 3 is a flow chart of the main diagnostic or tachycardia detection program embodied in the device illustrated in FIG. 4.

Those results were correlated and are depicted in FIG. 1 which is a reproduction of FIG. 3 from the article. FIG. 1 shows the changes in the sinus node rate as a function of time from onset of ventricular tachycardia during thirty-two episodes of hemodynamically stable ventricular tachycardia and twenty-one episodes of hemodynamically unstable ventricular tachycardia. The composite graphic data shows that beginning at about ten seconds after the onset of ventricular tachycardia, the atrial cycle length during unstable ventricular tachycardia began to increase rather than continue to shorten or stabilize. The inventor has developed a method and apparatus for recognizing the occurrence of physiological phenomenon and thereby allowing an automatic implantable pacemaker/cardioverter/defibrillator to more accurately chose appropriate antitachycardia treatment therapies for stable and unstable ventricular tachycardias.

Figure 2:
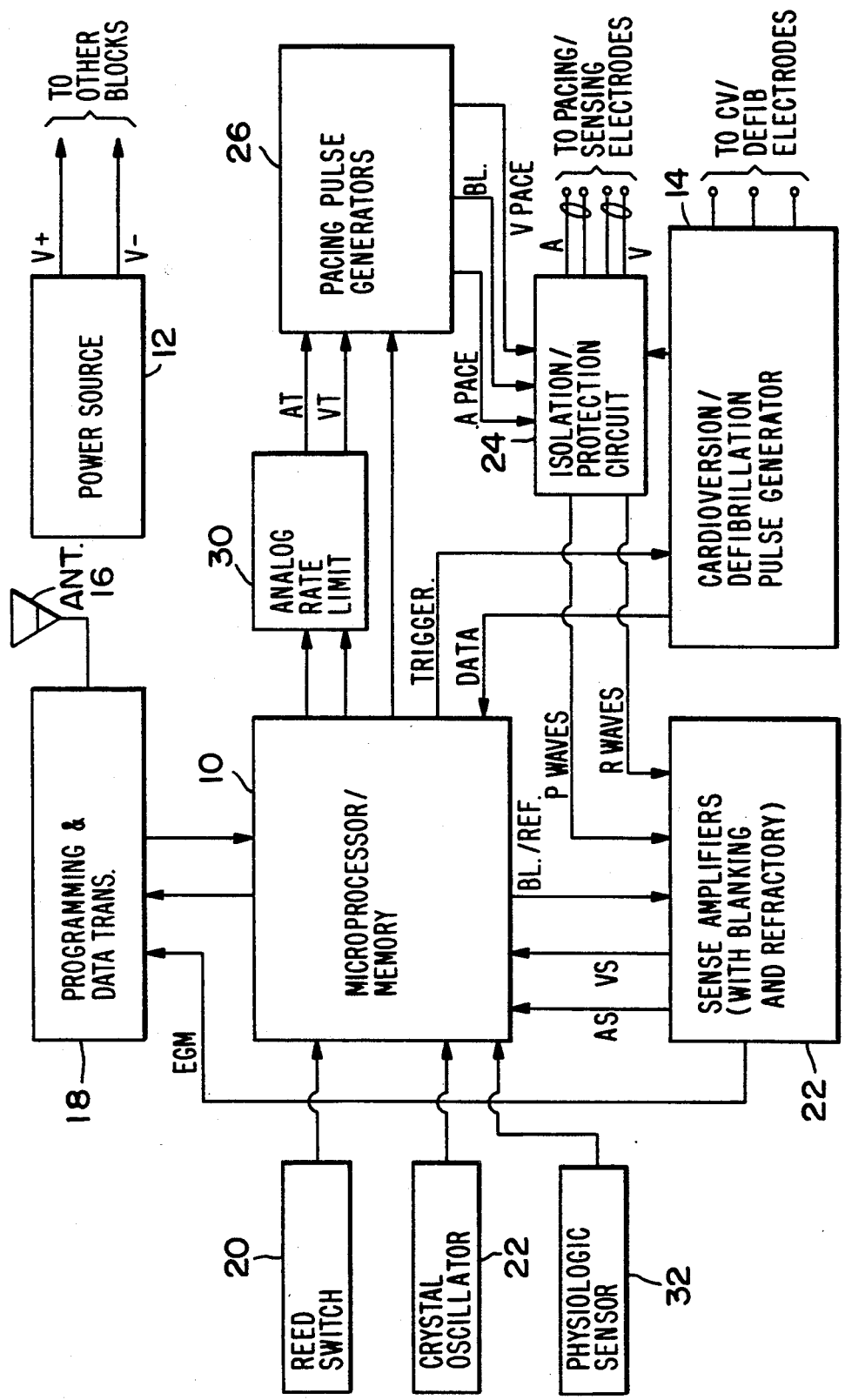
FIG. 2 is a block diagram representation of the electrical circuit of an implantable device in which the inventive detection and treatment method may be embodied.

Turning now to FIG. 2, a block diagram of the major components of automatic implantable device for detecting and treating brady and tachyarrhythmias is depicted. It is contemplated that such a device would be implemented in analog and digital microcircuits under the control of a central microprocessor/memory block 10 powered by a battery power source in block 12. The high power pulse generator block 14 would include the cardioversion/defibrillation pulse generator circuitry coupled by output terminals to two or more cardioversion/defibrillation electrodes to apply synchronized cardioversion or unsynchronized defibrillation shocks to the electrodes situated in or about the heart in a manner well known in the art.

It is contemplated that the implantable device depicted in FIG. 2 would function under the control of a resident operating program or software retained in memory within the microprocessor/control/memory block 10 and would be programmable by an external programmer/receiver (not illustrated in FIG. 4) communicating with the implanted device by radio frequency energy received or transmitted by antenna 16 under the control of the programming and data transmission block 18 and reed switch 20 which is responsive to an external magnet. The programming and data transmitting block 18 would be capable of receiving programming instructions and directing them to the memory within microprocessor/control/memory block 10 as well as transmitting data stored within the memory within block 10 as well as an electrogram representing the patient's atrial and ventricular activity in a manner well known in the pacing art.

For purposes of implementing the present invention, stored A—A and R—R intervals may be continually stored in portions of the memory within block 10 configured as circular buffers, such that at any given time, stored intervals indicative of the heart rhythm during at least the preceding several minutes are available for analysis. Following onset and detection of a ventricular rate indicative of a tachyarrhythmia, these stored intervals may be used to diagnose the origin of the tachyarrhythmia, and in conjunction with the present invention, are used to assess the hemodynamic stability of a rhythm identified as ventricular tachycardia.

The timing of all timing and processing functions, including the determination of atrial and ventricular cycle lengths, is controlled by counters within block 10 which measure and define time intervals under control of the microprocessor in block 10 and are driven by crystal oscillator 22 in a manner well known in the prior art of implantable digital pacemakers. The remaining blocks of FIG. 4 include the isolation/protection or interface block 2 which operates to direct atrial and ventricular pacing stimuli from the pacing pulse generator block 26 to respective atrial and ventricular output terminals which in turn are coupled through pacing leads to bipolar pacing electrodes situated in or near the atrium and ventricle of the heart, respectively. In addition, the interface 24 (when unblanked) couples the atrial and ventricular electrograms (or P-waves and R-waves respectively) to the sense amplifier block 28. Interface 24 is blanked or prevented from passing any signals picked up on the bipolar atrial and ventricular pacing/sensing electrodes to the sense amplifier block 28 during short blanking intervals following the delivery of an atrial or ventricular pacing stimulus in a fashion well known in the pacing art.

Furthermore, the interface 24 disconnects or shorts out the pacing/sensing electrodes during the delivery and for a short period after the delivery of a cardioversion/defibrillation shock by application of a control signal to the interface 24 by the cardioversion/defibrillation pulse generator block 14.

The P-waves and R-waves transmitted through the interface 24 to the sense amplifiers 28 are amplified and shaped to generate atrial and ventricular signals AS and VS, respectively, which are conducted to block 10 in order to derive the atrial and ventricular cycle lengths, the AV delay interval, and other intervals which may be appropriate to the overall function of the device. A further signal from a physiologic sensor 32 representative of cardiac or patient activity may also applied to the block 10 in order to control the bradyarrhythmia pacing rate in the DDDR or other rate responsive mode of operation and to augment detection of tachyarrhythmias.

The microprocessor within block i0 responds to atrial and ventrioular AS and VS signals and to the generation of atrial and ventricular pacing pulses by defining appropriate atrial and ventricular refractory and blanking intervals which are in turn communicated to the sense amplifier block 28 during certain windows of time following each respective AS and VS and following each pacing pulse in a fashion well known in the pacing art.

It is contemplated that the system depicted in FIG. 2 may be programmed to operate in any of the known bradycardia single or dual chamber pacing modes. The signal from the physiologic sensor 32 may be employed to modify the atrial and ventricular escape intervals to allow for a certain range of atrial and ventricular pacing depending upon the level of the patient's activity in a fashion well known in the bradycardia pacing art. The atrial and ventricular escape intervals established in memory are compared against the atrial and ventricular cycle lengths encountered in the patient and, if a bradycardia condition exists, the block 10 applies atrial and ventricular pace trigger signals AT and VT through analog rate limiter block 30 to the pacing pulse generator 26 which responds by developing the respective A pace and V pace signals. Analog rate limiter 30 operates telemetry atrial and ventricular pacing rates to a safe high rate into effect an appropriate upper rate behavior in the event that the spontaneous atrial rate exceeds the programmed upper rate limit in a fashion well known in the pacing art.

It is moreover contemplated that the microprocessor in block 10 may be programmed to provide a regimen of successive treatment therapies to treat any tachyarrhythmia that is not corrected to sinus rhythm by the delivery of the first therapy in the regimen. The successive therapies may be programmed to be more aggressive and may include both pacing energy and cardioversion defibrillation shock therapies.

Figure 4:
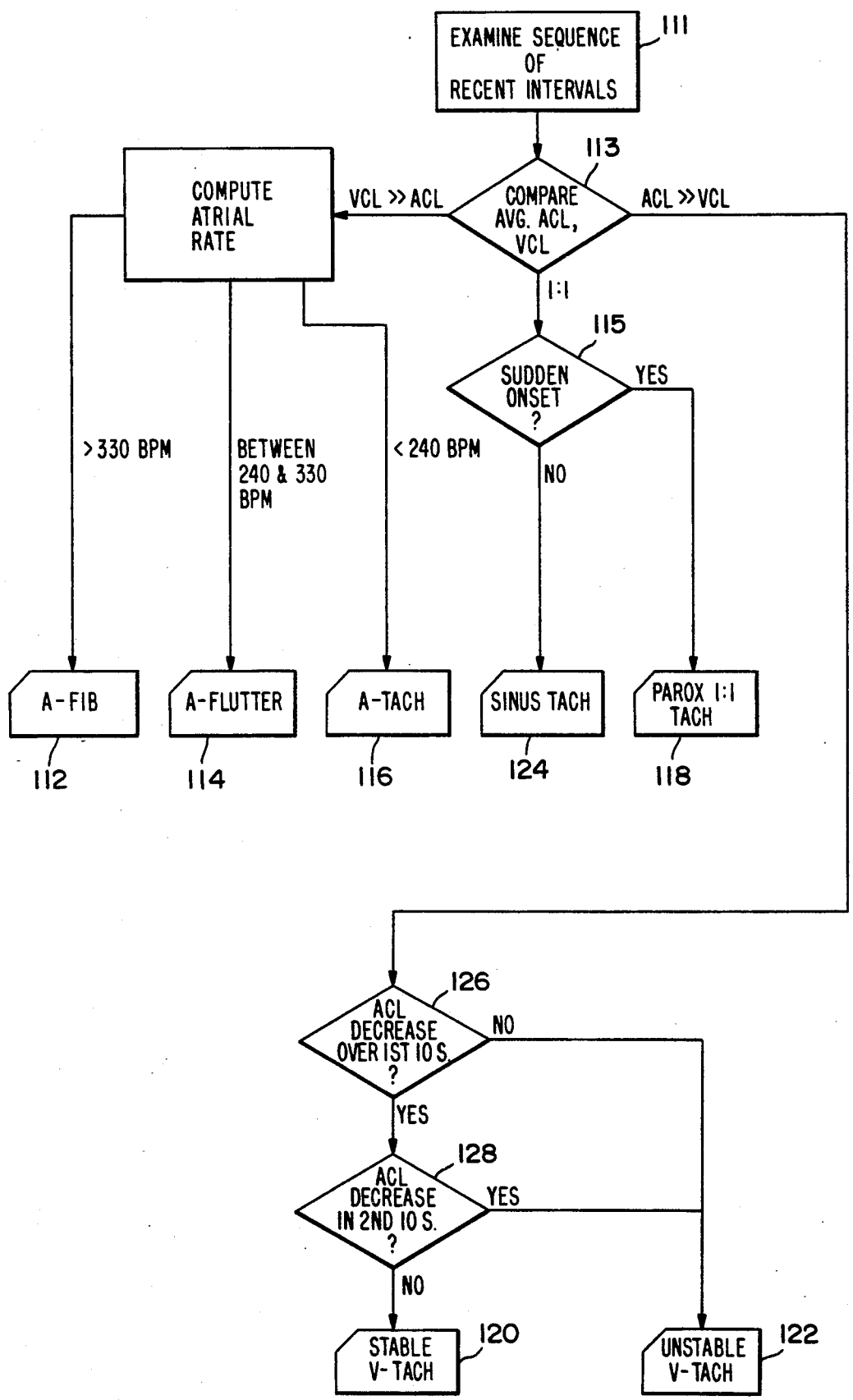
FIG. 4 is a flow chart of the tachycardia analysis function for recognizing and distinguishing stable and unstable ventricular tachycardias.

The system as described is rendered operational by resident software within the memory in block 10 which is capable of distinguishing normal sinus rhythm within the acceptable upper and lower rate limits of the main brady pacing routine and distinguishing various types of tachyarrhythmias in accordance with the overall program depicted in FIG. 3 and the tachycardia analysis routine depicted in FIG. 4.

FIG. 3 conforms generally to FIG. 1 of the aforementioned Arzbaecher et al artiCle and represents a generalized flow chart for tachycardia identification which detects a sustained fast rate in either the atrium or the ventricle and, in some cases awakens the tachycardia analysis program illustrated in FIG. 4 in order to conduct a detailed analysis of the tachycardia and its immediately preceding beats. FIG. 4 includes portion adapted from FIG. 2 of the Arzbaecher article with the addition of steps for discriminating stable from unstable ventricular tachycardia according to the present invention.

Referring to FIG. 3, it shows in block 100 the standby mode of operation of the microprocessor in orde to conserve power. When an AS or VS signal is received from the sense amplifier 28 of FIG. 2, it awakens the microprocessor in step 102 to compute the AA, VA, VV and AV intervals and store the most recent series of intervals, extending over the preceding several minutes, as depicted in block 104. In the event that a predetermined number of short intervals less than the tachycardia detection interval (TDI) or fibrillation detection interval (FDI) in either chamber occurs, during a predetermined time interval, tachyarrhythmia is detected at step 106 and the tachycardia analysis program of FIG. 4 is commenced. As long as tachyarrhythmia is not detected, the overall program continues to store the most recent intervals, discarding the oldest in turn.

FIG. 4 represents the tachycardia analysis program of the present invention. Its goal is to distinguish the tachyarrhythmias identified in blocks 112, 114, 116, 118, 120 and 122 from sinus tachycardia (block 124) and to direct the device depicted in FIG. 4 to apply the appropriate therapy or therapy regimens.

For example, atrial fibrillation (block 112), atrial flutter (block 114) and unstable ventricular tachycardia (block 122) would be treated by therapies including cardioversion and or defibrillation shocks (possibly preceded by a pacing therapy). However, atrial tachycardia (block 116), paroxysmal 1:1 tachycardia (block 118) and stable ventricular tachycardia (block 120) would be treated by one or more pacing therapies or regimens of pacing therapies, possibly followed by a cardioversion or defibrillation therapy if the pacing therapies were unsuccessful. Atrial flutter (block 114) may in some cases also, initially be treated by means of pacing therapies. Sinus tachycardia (block 124) would be untreated as it would be considered nonpathologic in nature.

The stored sequence of recent intervals indicative of the tachyarrhythmia is read from the memory in block 111 and the relative atrial and ventricular cycle lengths during a predetermined time period preceding the point at which the tachyarrhythmia detection criteria were satisfied are averaged and compared in block 113 to determine if the atrial cycle lengths have become shorter than or longer than the ventricular cycle lengths. If the atrial and ventricular cycle lengths have remained equal, then the sequence is examined to determine whether the onset of the tachycardia was gradual or sudden in block 115. For example, the first four beats satisfied the high rate condition may be compared to the four beats that preceded them, and if any has an inter-beat interval substantially shorter than the average of the four preceding beats, then the tachycardia is concluded to be paroxysmal with 1:1 conduction and paceterminable. Otherwise, the diagnosis is sinus tachycardia, a normal heart rhythm and no therapy is delivered.

In the event that the atrial cycle lengths are shorter than the ventricular cycle lengths, then the program compares the atrial cycle lengths against three threshold ranges and employs a rate based method to separate atrial tachycardia from atrial fibrillation and atrial flutter. If the atrial cycle lengths correspond to a rate exceeding 330 beats per minute, then it is concluded that atrial fibrillation exists. If the atrial cycle lengths correspond to a rate falling between 240 and 330 beats per minute, then atrial flutter is concluded to exist. Finally, if the atrial cycle lengths correspond to a rate less than 240 beats per minute (but, of course, exceeding the TDI), then it is concluded that an atrial tachycardia exists.

In the event that atrial fibrillation or atrial flutter are found, it is contemplated that the system detected in FIG. 2 would apply an appropriate shock between the pair of electrodes juxtaposed across the atrium of the heart. If atrial tachycardia is diagnosed, pacing therapies may be applied in an attempt to entrain or break the atrial tachycardia, and if that fails, cardioversion defibrillation shock may be delivered. As noted above, in some cases, pacing therapies might initially be attempted in cases of atrial flutter.

In the event that the ventricular cycle lengths are shorter than the atrial cycle lengths (i.e., the ventricular rate exceeds the atrial rate), the tachycardia analysis algorithm of FIG. 6 proceeds to a determination of whether or not the ventricular tachycardia is hemodynamically stable or unstable.

When a ventricular rate exceeds the atrial rate (generally by about 2–4:1) the sequence of intervals must be examined to determine whether or not the atrial rate increases during a first time period following the identified point of onset of the tachycardia. Onset may be identified by locating the first sequence of stored R-R intervals associated with the detected tachycardia exhibiting a rapid increase in ventricular rate. The first time period may be the first ten seconds following onset. If the atrial intervals exhibit this characteristic, the program then determines whether or not the atrial rate increases or decreases during a second time period, which may be the 10 seconds following the first time period.

If the atrial rate fails to increase during the first time period, or if it decreases during the second time period, then the program determines that the disassociated ventricular tachycardia is unstable and a cardioversion shock may be delivered, followed by further, higher energy synchronized or unsynchronized shocks if the initial shock is insufficient to break the tachycardia. However, if the atrial rate stabilizes or continues to increase during the second time period, then the program determines that the ventricular tachycardia is hemodynamically stable and one or more pacing therapies may be attempted.

In FIG. 4, block 126 determines whether the atrial cycle length decreases in the first ten seconds. If not, the tachycardia is diagnosed as unstable at 122. If so, then the program determines in block 128 whether the atrial cycle length increases in the second ten seconds. If so, then unstable ventricular tachycardia is diagnosed at 122. If not, stable ventricular tachycardia is diagnosed at 120.

The method set forth above treats stable atrial cycle lengths in the second time period as indicative of stable ventricular tachycardia, i.e, that failure to detect an increase in atrial cycle lengths is indicative of a hemodynamically stable ventricular tachycardia. However, a more conservative approach would be to regard stable atrial cycle lengths during the second time period as indicative of hemodynamically unstable ventricular tachycardia, i.e. that failure to continue to manifest a decrease in atrial cycle lengths during the second time period would trigger delivery of a cardioversion pulse. It is suggested that in commercial embodiments of a device according to the present invention, the treatment of a stable atrial cycle length during the second time period should be subject to programmer control and specified by the physician based on the condition of the particular patient. In either case, the detected increase of atrial cycle lengths during the second time period should be taken as indicative of hemodynamically unstable ventricular tachycardia and the detected continued decrese in atrial cycle lengths should be taken as indicative of hemodynamically stable ventricular tachycardia, for purposes of practicing the present invention.

Although a presently preferred embodiment of the invention has been described, it will be apparent from that description to those skilled in the field to which the invention pertains, that variations of the present embodiment may be implemented without departing from the principles of the invention. Further, as technological advances are made, for example, in developing practical small-size, low-cost high voltage components, similar to the advances in the semiconductor field, the principles of the invention may be applied directly to a "universal" implantable device for performing an all-purpose cardiac treatment function.

Accordingly, it is intended that the invention be limited not by the structural or functional elements of the described embodiment, but only as set out in the appended claims.

I claim:

1. A method of detecting and treating tachyarrhythmias of a living patient's heart comprising the steps of:

sensing the atrium and ventricle of the patient's heart and providing atrial (AS) and ventricular (VS) event detection signals;

measuring the time intervals (ACL's) between successive atrial event detection signals and the time intervals (VCL's) between successive ventricular event detection signals;

detecting the presence of tachycardia by comparing said VCL's to predetermined tachycardia detection criteria;

if tachycardia is detected, comparing said ACLs and VCLs with one another to determine whether said patient exhibits a greater ventricular than atrial rate during said detected tachycardia;

monitoring said ACL's during a predetermined time period during said detected tachycardia;

if said ACL's tend to shorten during said predetermined time period, delivering a first predetermined therapy to said patient's heart; and if said ACL's tend to lengthen during said predetermined time period during, delivering a second therapy differing from said first therapy to said patient's heart.

2. A method according to claim 1 wherein said step of comparing said ACL's and said VCL's comprises comparing averages of said ACL's and VCL's.

3. A method according to claim 1 wherein said first therapy comprises antitachycardia pacing.

4. A method according to claim 1 wherein said second therapy comprises a cardioversion pulse.

5. A method according to claim 1 or claim 2 or claim 3 or claim 4, wherein said monitoring step comprises the step of monitoring said ACL's during a first time period following onset of said detected tachycardia and during a second time period following said first time period.

6. A method according to claim 5 further comprising the step of delivering said second therapy if said ACL's do not decrease during said first time period.

7. A method according to claim 5 further comprising the step of delivering said second therapy if said ACL's increase during said second time period.

8. A method according to claim 5 wherein said first time period is about 10 seconds in duration.

9. A method according to claim 8 wherein said second time period is about 10 seconds in duration.

10. An apparatus for detecting and treating tachyarrhythmias of a living patient's heart comprising:
- means for sensing the atrium and ventricle of the patient's heart and providing atrial (AS) and ventricular (VS) event detection signals;
- means for measuring and storing the time intervals (ACL's) between successive atrial event detection signals and the time intervals (VCL's) between successive ventricular event detection signals;
- means for detecting the presence of tachycardia by comparing the measured VCL's to predetermined tachycardia detection criteria;
- means for comparing said stored ACLs and VCLs with one another if tachycardia is detected, to determine whether said patient exhibits a greater ventricular than atrial rate during said detect tachycardia;
- means for defining a predetermined time period during said detected tachycardia;
- means for monitoring the patient's ACLs during said predetermined time period, if said ventricular rate is greater than said atrial rate;
- means for delivering a first predetermined therapy to said patient's heart if said ACL's tend to shorten during said predetermined time period; and
- means for delivering a second therapy differing from said first therapy to said patient's heart if said ACL's tend to lengthen during said predetermined time period.

11. An apparatus according to claim 10 wherein said means for comparing said ACL's and said VCL's comprises means for comparing averages of said ACL's and VCL's.

12. An apparatus according to claim 11 wherein said first therapy comprises antitachycardia pacing.

13. An apparatus according to claim 11 wherein said second therapy comprises a cardioversion pulse.

14. An apparatus according to claim 10 or claim 11 or claim 12 or claim 13, further comprising means for defining a first time period following onset of said detected tachycardia and a second time period following said first time period.

15. An apparatus according to claim 14 further comprising means for delivering said second therapy if said ACL's do not decrease during said first time period.

16. An apparatus according to claim 14 further comprising means for delivering said second therapy if said ACL's increase during said second time period.

17. An apparatus according to claim 14 wherein said first time period is about 10 seconds in duration.

18. An apparatus according to claim 17 wherein said second time period is about 10 seconds in duration.

* * * * *